United States Patent
Watanabe

(10) Patent No.: US 9,682,166 B2
(45) Date of Patent: Jun. 20, 2017

(54) ADDITIVE MANUFACTURING POWDER AND METHOD OF MANUFACTURING THE SAME

(71) Applicant: Masaki Watanabe, Kanagawa (JP)

(72) Inventor: Masaki Watanabe, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 14/814,839

(22) Filed: Jul. 31, 2015

(65) Prior Publication Data

US 2016/0038633 A1    Feb. 11, 2016

(30) Foreign Application Priority Data

Aug. 11, 2014  (JP) ................. 2014-163425
May 15, 2015  (JP) ................. 2015-099999

(51) Int. Cl.

| | | |
|---|---|---|
| *A61L 27/18* | (2006.01) | |
| *A61L 27/12* | (2006.01) | |
| *A61L 27/08* | (2006.01) | |
| *A61L 27/50* | (2006.01) | |
| *B29C 67/00* | (2017.01) | |
| *C04B 35/634* | (2006.01) | |
| *G03G 9/08* | (2006.01) | |
| *G03G 9/093* | (2006.01) | |
| *C04B 35/447* | (2006.01) | |
| *C04B 35/52* | (2006.01) | |
| *C04B 35/528* | (2006.01) | |
| *C04B 35/628* | (2006.01) | |
| *B33Y 80/00* | (2015.01) | |
| *B33Y 10/00* | (2015.01) | |
| *B29K 67/00* | (2006.01) | |
| *B29K 33/00* | (2006.01) | |
| *B29K 25/00* | (2006.01) | |

(52) U.S. Cl.

CPC .............. *A61L 27/18* (2013.01); *A61L 27/08* (2013.01); *A61L 27/12* (2013.01); *A61L 27/50* (2013.01); *B29C 67/0077* (2013.01); *C04B 35/447* (2013.01); *C04B 35/522* (2013.01); *C04B 35/528* (2013.01); *C04B 35/62802* (2013.01); *C04B 35/6346* (2013.01); *C04B 35/63424* (2013.01); *C04B 35/63432* (2013.01); *G03G 9/0819* (2013.01); *G03G 9/0827* (2013.01); *G03G 9/09321* (2013.01); *G03G 9/09371* (2013.01); *G03G 9/09392* (2013.01); *A61L 2400/12* (2013.01); *A61L 2430/02* (2013.01); *B29K 2025/04* (2013.01); *B29K 2033/08* (2013.01); *B29K 2067/00* (2013.01); *B33Y 10/00* (2014.12); *B33Y 80/00* (2014.12); *C04B 2235/3212* (2013.01); *C04B 2235/425* (2013.01); *C04B 2235/5288* (2013.01); *C04B 2235/5296* (2013.01); *C04B 2235/5436* (2013.01); *C04B 2235/5481* (2013.01); *C04B 2235/6026* (2013.01); *C04B 2235/665* (2013.01); *C04B 2235/9638* (2013.01)

(58) Field of Classification Search

CPC .......... A61L 27/18; A61L 27/08; A61L 27/12; A61L 27/50; A61L 2400/12; A61L 2430/02; B29C 67/0077; C04B 35/447; C04B 35/522; C04B 35/528; C04B 35/62802; C04B 35/63424; C04B 35/63432; C04B 35/6346; C04B 2235/3212; C04B 2235/425; C04B 2235/5288; C04B 2235/5296; C04B 2235/5436; C04B 2235/5481; C04B 2235/6026; C04B 2235/665; C04B 2235/9638; G03G 9/0819; G03G 9/0827; G03G 9/09321; G03G 9/09371; G03G 9/09392; B33Y 10/00; B33Y 80/00; B29K 2025/04; B29K 2033/08; B29K 2067/00

See application file for complete search history.

(56) References Cited

U.S. PATENT DOCUMENTS

| | | | |
|---|---|---|---|
| 5,204,055 | A | 4/1993 | Sachs et al. |
| 5,902,441 | A | 5/1999 | Bredt et al. |
| 6,322,728 | B1 | 11/2001 | Brodkin et al. |
| 6,375,874 | B1 | 4/2002 | Russell et al. |
| 2002/0064745 | A1 | 5/2002 | Schulman et al. |
| 2009/0186289 | A1 | 7/2009 | Nakamura et al. |
| 2010/0239974 | A1 | 9/2010 | Nozaki et al. |
| 2013/0130171 | A1 | 5/2013 | Watanabe et al. |
| 2014/0356441 | A1 | 12/2014 | Watanabe et al. |

FOREIGN PATENT DOCUMENTS

| | | |
|---|---|---|
| JP | 5-031166 | 2/1993 |
| JP | 9-324203 | 12/1997 |
| JP | 2000-328106 | 11/2000 |

(Continued)

OTHER PUBLICATIONS

Extended European Search Report issued on Dec. 1, 2015 in European Patent Application No. 15179307.2.

*Primary Examiner* — Nathan M Nutter

(74) *Attorney, Agent, or Firm* — Oblon, McClelland, Maier & Neustadt, L.L.P.

(57) ABSTRACT

Additive manufacturing powder contains a core-shell type particle containing a core particle comprising a first binder resin and a filler and a shell present on the surface of the core particle. The shell contains a second binder resin. The powder has a particle size distribution Dv/Dn of 1.5 or less and an average circularity of from 0.800 to 0.980, the average circularity being represented by the following relation:

Average circularity=(a perimeter of a circle having the same area as a projected image of a particle)/(the perimeter of the projected image of the particle)×100.

15 Claims, No Drawings

(56) References Cited

FOREIGN PATENT DOCUMENTS

| | | |
|---|---|---|
| JP | 2004-042546 | 2/2004 |
| JP | 2004-069403 | 3/2004 |
| JP | 2004-202126 | 7/2004 |
| JP | 3607300 | 10/2004 |
| JP | 2009-156902 A | 7/2009 |
| JP | 4575295 | 8/2010 |
| WO | WO98/09798 A1 | 3/1998 |
| WO | WO2005/011536 A1 | 2/2005 |

ADDITIVE MANUFACTURING POWDER AND METHOD OF MANUFACTURING THE SAME

CROSS-REFERENCE TO RELATED APPLICATIONS

This patent application is based on and claims priority pursuant to 35 U.S.C. §119 to Japanese Patent Application Nos. 2014-163425 and 2015-099999, on Aug. 11, 2014 and May 15, 2015, respectively, in the Japan Patent Office, the entire disclosures of which are hereby incorporated by reference herein.

BACKGROUND

Technical Field

The present invention relates to additive manufacturing powder and a method of manufacturing the additive manufacturing powder.

Background Art

A group of technologies to manufacture three-dimensional objects using solid form data created by three dimensional computer aided design system (3D CAD), etc. is referred to as rapid prototyping technologies. By using molding technique for heat-resisting powder of these technologies, molds or cores can be manufactured without using a model or pattern so that casting production processes becomes extremely short. The rapid prototyping technologies are also referred to as additive manufacturing methods, by which a 3D object is produced by laminating cross sections thereof. In addition, the rapid prototyping technologies includes various layer manufacturing methods (powder fixing methods) using powder as a material.

Conventionally, artificial bones are made of metal materials such as stainless and titanium alloy and abrasion resisting plastic and used for bone replacement operation. These artificial bones substitute malfunctioning joints to fulfill joint function. However, metal materials and wear resistant plastic deteriorate with age due to abrasion, corrosion, swelling, etc. so that they are not suitable for use for a long period of time. Ceramics based on calcium phosphate are now used instead of these materials. Currently, such ceramics are used to provide a scaffold to form bones or promote formation of new bones while being absorbed in bones with time to be substituted with the bones in the future.

As bone prosthetic materials to provide a scaffold for bone formation, for example, materials such as hydroxyapatite having excellent affinity with bone tissue and directly bondable with bone tissue without inclusion are used in many cases. By embedding the bone prosthetic material into the bone defect portion, bone repair is conducted quickly using the bone prosthetic material as a scaffold.

However, bone replacement does not occur by simple hydroxyapatite, hyroxyapatite remaining in a biological body may cause a problem. On the other hand, when the bone prosthetic material with which substitutes bones is embedded into bone tissue, osteogenetic function of the bone tissue is promoted, so that the bone is repaired more easily and more quickly.

As the bone prosthetic material with which bones are substituted, a specific example thereof is tricalcium phosphate (TCP). The degree of tricalcium phosphate absorbed in bones depends on the form of tricalcium phosphate compact. That is, porous tricalcium phosphate has large specific surface area in terms of form and are easily absorbed in bone tissue and are vulnerable to attack of phagocytic cells. To the contrary, dense tricalcium phosphate is extremely slowly absorbed and not easily attacked by phagocytic cells. By combining porous portions and dense portions utilizing such form differences, expression of desired biological compatibility is expected. However, such a combined material is not strong enough to be applied to bones such as thighbone receiving heavy burden. Moreover, it takes longer hours to mold and process the material into a desired form and in particular in the case of a structure having an inside structure, fine processing is impossible by cutting (slicing).

These powder additive manufacturing methods are advantageous in terms of fine processing but requires some devisal to shape a material such as ceramics or carbon fiber which has an extremely high melting point and is not melted by typical laser beams

SUMMARY

The present invention provides an improved additive manufacturing powder contains a core-shell type particle containing a core particle comprising a first binder resin and a filler and a shell present on the surface of the core particle. The shell contains a second binder resin. The powder has a particle size distribution Dv/Dn of 1.5 or less and an average circularity in the range of from 0.800 to 0.980, the average circularity being represented by the following relation:

Average circularity=(a perimeter of a circle having same area as a projected image of a particle)/ (the perimeter of the projected image of the particle)×100.

DETAILED DESCRIPTION

JP-2004-69403-A1 discloses "METHOD AND APPARATUS FOR STEREOSCOPICALLY COLOR COPYING" which includes a sample section imaging step (A) of imaging a two-dimensional image of a cut section by cutting the sample, by sequentially pushing the sample in a predetermined direction, a data processing step (B) of calculating a three-dimensional internal structure of the sample from the image and converting the structure into data which can be color rapid prototyped, and a stereoscopically color model manufacturing step (C) of manufacturing the stereoscopic color model by using a color rapid prototyping unit.

Moreover, U.S. Pat. No. 6,322,728 discloses "Mass production of dental restoration by solid free-form fabrication methods" which includes (a) depositing a layer of ceramic or composite material;
(b) applying a bonding material onto the ceramic or composite layer;
(c) repeating steps (a) and (b) a number of times to produce a number of layers of ceramic or composite material which are bonded to one another to form a shape of a dental restoration; and
(d) curing the shaped material to form the dental restoration.

US patent application No. 2002-0034675 discloses "Mass production of shells and models for dental restorations produced by solid free-form fabrication methods" which includes (a) using digitized data to provide a shape for the shell; (b) depositing a layer of polymeric material; and (c) repeating step (b) a number of times to produce a number of layers of the polymeric material which are bonded to one another to form the shape of the shell based on the digitized data.

Moreover, JP-2004-202126-A discloses "A method for manufacturing artificial bone" which includes: a step of sending a powder biomaterial and a liquid biomaterial to near the nozzle tip of a spraying device through separate passages, a step of jetting the mixture of the biomaterials out of the nozzle to a solid surface to form a layer by attaching the mixture to the surface, and a step of repeating jetting the powder biomaterial and the liquid biomaterial to form multiple attachment layers, whereby an artificial bone of three-dimensional structure.

In addition, WO2005011536 discloses "An artificial bone forming method", which includes a powder layer forming step for laminating powder layers using a powder bone hardened by hydration to mold a more strengthened artificial bone. However, strength is not secured sufficiently by such curing by hydration so that it is difficult to use such artificial bones as in particular bones such as thighbones receiving heavy burden.

"A method for manufacturing artificial bone" or "An artificial bone forming method" is also referred to as inkjet type powder additive manufacturing.

The present invention is to provide additive manufacturing powder that can fabricate a laminate object having a complex solid free form with high level of mechanical strength and good dimension accuracy.

The additive manufacturing powder and the method of manufacturing an additive manufacturing object using the additive manufacturing powder are described in detail below. Incidentally, it is to be noted that the following embodiments are not limiting the present disclosure and any deletion, addition, modification, change, etc. can be made within a scope in which man in the art can conceive including other embodiments, and any of which is included within the scope of the present disclosure as long as the effect and feature of the present disclosure are demonstrated.

An embodiment of the additive manufacturing powder of the present disclosure contains a core-shell type particle containing a core particle containing a first binder resin and a filler and a shell present on the surface of the core particle. The shell contains a second binder resin. The powder has a particle size distribution Dv/Dn of 1.5 or less and an average circularity in the range of from 0.800 to 0.980. The average circularity is represented by the following relation.

Additive Manufacturing Powder

The additive manufacturing powder of the present disclosure contains a core-shell type particle containing a core particle containing a first binder resin and a filler and a shell present on the surface of the core particle. The shell contains a second binder resin. The powder has a particle size distribution Dv/Dn of 1.5 or less and an average circularity in the range of from 0.800 to 0.980. The average circularity is represented by the following relation.

Average circularity=(a perimeter of a circle having a same area as that of a projected image of a particle)/(the perimeter of the projected image of the particle)×100.

An embodiment of the additive manufacturing powder of the present disclosure is described below. A solution or liquid dispersion is prepared in which the core particle containing the first binder resin (e.g., polyester resin) and the filler (e.g., calcium phosphate based material, carbon based material) are dissolved or dispersed in an organic solvent. The solution or liquid dispersion is added to, for example, to an aqueous medium containing the second binder resin (e.g., styrene-acrylic resin) having an average particle diameter in the range of from 20 nm to 60 nm to prepare an emulsion or liquid dispersion. Thereafter, by removing the organic solvent from the emulsion or the liquid dispersion to form particles (core-shell type particle) for additive manufacturing, the additive manufacturing particles are dispersed by deionized water to prepare a liquid dispersion. Moreover, the liquid dispersion is heated while being stirred to obtain additive manufacturing powder.

The thus-obtained additive manufacturing powder contains a core-shell type particle including the shell containing the second binder resin present on the surface of the core particle containing the first binder resin and the filler. The core particle can be covered with the shell or the shell can adhere to the core particle.

Binder Resin

In the core-shell type particle, the first binder resin is contained in the core particle and the second binder resin is contained in the shell. In the present disclosure, it is preferable that the second binder resin is incompatible with the first resin and swelling to ethyl acetate.

In addition, as described in detail below, the first binder resin is preferably a polyester resin and the second binder resin is a styrene-acrylic resin.

First Binder Resin

As the first binder resin, it is preferable for the first binder resin to have a wavelength that absorbs a laser beam used during additive manufacturing and emulsification property. The first binder resin can be selected to a particular application. Of these, a polyester resin is preferable. As the first binder resin, multiple resins can be combined. Moreover, it is also preferable to have near 1,000 cm$^{-1}$ as the absorption wavelength in the case of, for example, $CO_2$ laser.

As the polyester-based resin for use in the present disclosure, it is possible to use a resin obtained by polyesterification of at least one polyol represented by the following chemical formula 1 and at least one polycarboxylic acid represented by the following chemical formula 2.

A-(OH)$m$         Chemical formula 1

In the Chemical formula 1, a symbol "A" represents an alkyl group having 1 to 20 carbon atoms, an alkylene group, a substituted or non-substituted aromatic group, or a substituted or non-substituted heterocyclic aromatic group. A symbol "m" represents an integer in the range of from 2 to 4.

B—(COOH)$n$        Chemical formula 2

In the Chemical formula 2, a symbol "B" represents an alkyl group having 1 to 20 carbon atoms, an alkylene group, a substituted or non-substituted aromatic group, or a substituted or non-substituted heterocyclic aromatic group. A symbol "n" represents an integer in the range of from 2 to 4.

Specific examples of the polyol represented by Chemical formula 1 include, but are not limited to, ethylene glycol, diethylene glycol, triethylene glycol, 1,2-propylene glycol, 1,3-propylene glycol, 1,4-butane diol, neopentyl glycol, 1,4-butene diol, 1,5-pentane diol, 1,6-hexane diol, 1,4-cyclohexane dimethanol, dipropylene glycol, polyethylene glycol, polypropylene glycol, polytetramethylene glycol, sorbitol, 1,2,3,6-hexanetetrol, 1,4-sorbitan, pentaerythritol, dipentaerythritol, tripentaerythritol, 1,2,4-butane triol, 1,2,5-pentane triol, glycerol, 2-methylpropane triol, 2-methyl-1,2,4-butane triol, trimethylol ethane, trimethylol propane, 1,3,5-trihydroxy benzene, bisphenol A, an adduct of bisphenol A with propylene oxide, hydrogenated bisphenol A, an adduct of hydrogenated bisphenol A with ethylene oxide, and an adduct of hydrogenated bisphenol A with propylene oxide.

Specific examples of the polycarboxylic acid represented by Chemical formula 2 include, but are not limited to, maleic acid, fumaric acid, citraconic acid, itaconic acid, glutaconic acid, phthalic acid, isophthtalic acid, terephthalic acid, succinic acid, adipic acid, sebacic acid, azelaic acid, maronic acid, n-dodecenyl succinic acid, isooctyl succinic acid, isododecenyl succinic acid, n-octenyl succinic acid, n-octyl succinic acid, isooctenyl succinic acid, 1,2,4-benzene tricarboxylic acid, 2,5,7-naphthalene tricarboxylic acid, 1,2,4-naphthalene tricarboxylic acid, 1,2,4-butane tricarboxylic acid, 1,2,5-hexane tricarboxylic acid, 1,3-dicarboxyl-2-methyl-2-methylene carboxy propane, 1,2,4-cyclohexane tricarboxylic acid, tetra(methylenecarboxyl)methane, 1,2,7,8-octane tetracarboxylic acid, pyromellitic acid, Empol® trimer acid, cyclohexane dicarboxylic acid, cyclohexene dicarboxylic acid, butane tetracarboxylic acid, diphenyl sulfone tetracarboxylic acid, and ethylene glycol bis(trimellitic acid).

It is preferable that the polyester resin satisfies the following requisites.

The glass transition temperature thereof is preferably from 30 degrees C. to 80 degrees C.

The acid value of the polyester resin is preferably from 10 mgKOH/g to 30 mgKOH/g.

The weight average molecular weight Mw of polyester resin is preferably from 4,000 to 20,000.

The content of the polyester resin to the additive manufacturing powder is preferably from 1 percent by weight to 50 percent by weight.

Within this range, the polyester resin fulfills the features as binder resin.

In addition, in addition to the polyester resins specified above, for example, polyols can also be used.

Second Binder Resin

The second binder resin can be any rein that can form an aqueous liquid dispersion in an aqueous medium. The second binder resin can be selected to a specific application from known resins without a particular limitation. Of these, styrene-acrylic resins are preferable.

Styrene-acrylic resins can be thermoplastic resins or thermocurable resins. Specific examples thereof include, but are not limited to, vinyl resins, polyurethane resins, epoxy resins, polyester resins, polyamide resins, polyimide resins, silicone resins, phenolic resins, melamine resins, urea resins, aniline resins, ionomer resins, and polycarbonate resins. These can be used alone or in combination.

Of these resins, it is preferable to use at least one kind of resin selected from the group consisting of vinyl resins, polyurethane resins, epoxy resins, and polyester resins to form the second resin because an aqueous liquid dispersion including fine spherical particles can be easily prepared. Specific examples of the vinyl resins include, but are not limited to, polymers, which are prepared by polymerizing a vinyl monomer or copolymerizing vinyl monomers, such as styrene-(meth)acrylate resins, styrene-butadiene copolymers, (meth)acrylic acid-acrylate copolymers, styrene-acrylonitrile copolymers, styrene-maleic anhydride copolymers, and styrene-(meth)acrylic acid copolymers.

Anionic styrene-acrylic resins are preferable. Such styrene-acrylic resins are manufactured by using an anionic activator or introducing an anionic group such as a carboxylic acid group or a sulfonic acid group into a resin in the method specified later. It is preferable that styrene-acrylic resins have particle forms. The average primary particle diameter thereof is preferably from 20 nm to 60 nm to control the particle diameter and the particle size distribution of emulsified particles. More preferably, the particle diameter ranges from 30 nm to 50 nm.

The particle diameter can be measured by scanning electron microscopy (SEM), transmission electron microscopy (TEM), a light scattering method, etc. Preferably, using LA-920 (manufactured by Horiba Ltd.) according to a laser scattering measuring method, the particle diameter is measured after suitable dilution for an appropriate measuring range. The volume average particle diameter is measured as the particle diameter.

Styrene-acrylic resin particulates can be obtained through polymerization using any suitably selected known method. It is preferred to obtain as an aqueous liquid dispersion of styrene-acrylic resin particulates. For example, as the method of preparing an aqueous liquid dispersion of the styrene-acrylic resin particulates, the following methods are suitable.

(1) In a case of a vinyl resin, a method of manufacturing an aqueous liquid dispersion of styrene-acrylic resin particulates directly from the polymerization reaction by a suspension polymerization method, an emulsion polymerization method, a seed polymerization method, or a dispersion polymerization method using a vinyl monomer as the starting material of the resin particulates.

(2) In a case of a polyaddition-based or polycondensation-based resin such as a polyester resin, a polyurethane resin, and an epoxy resin, a method of manufacturing an aqueous liquid dispersion of styrene-acrylic resin particulates by: dispersing a precursor (monomer, oligomer, etc.) or its solvent solution under the presence of a suitable dispersion agent; curing the liquid dispersion by heating or addition of a curing agent.

(3) In a case of a polyaddition or polycondensation resin such as a polyester resin, a polyurethane resin and an epoxy resin, a method of manufacturing an aqueous liquid dispersion of resin particulates by dissolving a suitable emulsification agent in a precursor (monomer, oligomer, etc.) or its solvent solution (liquid is preferred, possibly liquidized by heating) followed by adding water for phase change emulsification.

(4) A method of pulverizing a resin preliminarily manufactured by a polymerization reaction (addition polymerization, ring scission polymerization, polyaddition, addition condensation, polycondensation, etc.) with a fine grinding mill of a mechanical rotation type or jet type, classifying the resultant to obtain styrene-acrylic resin particulates, and dispersing the resin particulates in water under the presence of a suitable dispersant.

(5) A method of spraying a resin solution in which a preliminarily manufactured resin by a polymerization reaction (addition polymerization, ring scission polymerization, polyaddition, addition condensation, polycondensation, etc.) is dissolved in a solvent in a form of a fine liquid mist to obtain styrene-acrylic resin particulates followed by dispersion thereof in water under the presence of a suitable dispersant.

(6) A method of adding a poor solvent to a resin solution in which a preliminarily manufactured resin by a polymerization reaction (addition polymerization, ring scission polymerization, polyaddition, addition condensation, polycondensation, etc.) is dissolved in a solvent or cooling-down of a resin solution preliminarily prepared by dissolving the resin in a solvent by heating to precipitate styrene-acrylic resin particulates; removing the solvent to obtain the resin particulates; and dispersing them in water under the presence of a suitable dispersant.

(7) A method of dispersing a resin solution in which a preliminarily manufactured resin by a polymerization reaction (addition polymerization, ring scission polymerization, polyaddition, addition condensation, polycondensation, etc.) is dissolved in a solvent in an aqueous medium under the presence of a suitable dispersant; and removing the solvent by heating, reduced pressure, etc.

(8) A method of dissolving a suitable emulsifying agent in a resin solution in which a preliminarily manufactured resin by a polymerization reaction (addition polymerization, ring opening polymerization, polyaddition, addition condensation, polycondensation, etc.) is dissolved in a solvent; and adding water to the solution for phase change emulsification.

It is preferable that styrene-acrylic resins satisfy the following requisites.

The glass transition temperature thereof is preferably from 30 degrees C. to 80 degrees C.

The acid value of styrene-acrylic resin is preferably from 150 mgKOH/g to 250 mgKOH/g.

The weight average molecular weight Mw of styrene-acrylic resin is preferably from 200,000 to 800,000.

The content of styrene-acrylic resin to the additive manufacturing powder is preferably from 0.01 percent by weight to 0.05 percent by weight.

When these ranges are satisfied, the binder resin can be turned into particles.

Moreover, the acid value of the styrene-acrylic resins is preferably greater than that of the polyester resins.

As described above, it is preferable that the second binder resin is incompatible with the first resin and swelling to ethyl acetate. Evaluation of the swelling of the second resin to ethylacetate is described below using the styrene-acrylic resin as an example.

Styrene-acrylic resin as the second binder resin is added to a screw vial (30 mL, manufactured by AS ONE Corporation.) in such a manner that the resins reaches 20 mL from the bottom followed by charging of 10 mL of ethyl acetate with pipette. Thereafter, the system is left still for 24 hours to phase-separate an emulsion of white resin particulates to bottom and ethylacetate to top. Swelling to ethylacetate is evaluated by observing the height of the white resin particulate emulsion from the bottom of the screw vial. As swelling becomes high, the height increases. The height is preferably 20 mm or greater and more preferably 21 mm or greater.

In addition, other than the styrene-acrylic resins specified above, for example, styrene resins, etc. can also be used.

Filler

Fillers contained in a core particle can be any material constituting a desired (sintered) object of additive manufacturing. Inorganic materials are preferable. Moreover, carbon materials are preferable to obtain a light-weight and strong object. The carbon materials are formed of only carbon, i.e., isotopes. Calcium phosphate is preferable to manufacture an artificial bone. These can be used in combination.

The content of the filler to the additive manufacturing powder of the present disclosure is changeable depending on the purpose and the identity of the filler. To reduce the loss of a resin during laser irradiation and improve the dimension accuracy, the content of the filler is preferably from 30 percent by weight or greater to the additive manufacturing powder, more preferably from 35 percent by weight or greater, and furthermore preferably from 40 percent by weight or greater. There is no specific upper limit but 60 percent by weight or less is preferable.

Moreover, the volume average particle diameter A of the filler and the volume average particle diameter B of the additive manufacturing powder satisfy the following relation:

Preferably, A/B<0.8
More preferably to improve granularity, A/B<0.7
Furthermore preferably, A/B<0.6.

There is no specific lower limit but 0.2 or greater is preferable. The volume average particle diameter is obtained by the method described later.

Calcium phosphate and carbon material are described in detail.

Calcium Phosphate

There is no specific limit to calcium phosphate the having a particle form or powder form. It can be selected to a particular application.

Specific examples of the materials for calcium phosphate include, but are not limited to, hydroxyapatite (HAp), carbonate apatite, fluoroapatite, α-tricalcium phosphate (α-TCP), β-tricalcium phosphate (β-TCP), tetracalcium phosphate, and octacalcium phosphate (OCP). These can be used alone or in combination.

Of these, in terms of obtaining an additive manufacturing object (solid free form) replaced with bones, hydroxyapatite (HAp), α-tricalcium phosphate (α-TCP), β-tricalcium phosphate (β-TCP), and octacalcium phosphate (OCP) are preferable.

It is possible to use particles or powder of products available on market formed of these materials as the calcium phosphate. Specific examples of the products include, but are not limited to, α-TCP and β-TCP. Calcium phosphate treated with known surface (modification) treatment can be also used to improve agglomeration property.

There is no specific limit to the manufacturing method of the calcium phosphate. It can be selected to a particular application. For example, precipitation method, etc. are used, which are suitably used in synthesis of hydroxyapatite (HAp).

Carbon Material

There is no specific limit to the carbon material. It can be suitably selected to a particular application. For example, the content of carbon is preferably in the range of from 85 percent by weight to 100 percent by weight. Specific examples thereof include, but are not limited to, polyacrylonitrile (PAN) based carbon fiber, rayon-based carbon fiber, lignin-based carbon fiber, pitch-based carbon fiber, vapor-grown carbon fiber, carbon black, fullerene, graphene, carbon nanotube, and carbon nanohorn.

Of these, fullerene, graphene, carbon nanotube are preferable.

There is no specific limit to the form and structure of the carbon material. It can be suitably selected to a particular application. In terms of forms, for example, multi-layer carbon nanotube and single-layered carbon nanotube are suitable. When it comes to size, sub-micron order is preferable at most considering being encapsulated in the first binder resin (for example, polyester resin).

Other Components

There is no specific limitation to the selection of the other known components that can be contained in the additive manufacturing powder. A suitable component can be selected to a particular application. Specific examples thereof include, but are not limited to, a chelate agent, fluidizer, a leveling agent, and a sintering additive.

Adding a fluidizer to the additive manufacturing powder is preferable because layers of the additive manufacturing powder are efficiently formed with ease.

Adding a leveling agent to the additive manufacturing powder is preferable because the wettability of the additive manufacturing powder is improved, so that handling becomes easy.

Adding a sintering additive to the additive manufacturing powder is preferable because sintering at lower temperatures is made possible in sintering treatment for obtained cured material (additive manufacturing object and cured material for sintering).

Property of Additive Manufacturing Powder

The volume average particle diameter Dv of the additive manufacturing powder preferably ranges from 4.0 μm to 10.0 μm and more preferably from 4.5 μm to 7.0 μm. When the volume average particle diameter Dv is 4.0 μm or greater, it is possible to suppress the interparticle action and agglomeration property, thereby improving the manufacturing efficiency of additive manufacturing object. To the contrary, when a thin layer is formed using the additive manufacturing powder having a volume average particle diameter Dv 10.0 μm or less, it is possible to increase the filling rate of the additive manufacturing powder in the thin layer, meaning reducing the void rate, so that the voids in the additive manufacturing object can be reduced. Incidentally, the average particle diameter of the additive manufacturing powder can be adjusted by the conditions of emulsification and/or dispersion by stirring, etc. of an aqueous medium in the emulsification process.

The volume average particle diameter of the additive manufacturing powder can be measured according to known methods using a known particle diameter measuring instrument such as Multisizer III (manufactured by Beckman Coulter, Inc.) and FPIA 3000 (manufactured by Sysmex Corporation).

The particle size distribution Dv/Dn, the rate of the volume average particle diameter Dv to the number average particle diameter Dn, is 1.5 or less, preferably 1.25 or less, and more preferably 1.15 or less. When the particle size distribution Dv/Dn surpasses 1.5, coarse particles may cause noises when forming a thin layer of the additive manufacturing powder and also fine powder increases, which may promote self agglomeration.

The particle size distribution Dv/Dn of the additive manufacturing powder can be measured according to known methods using a known particle diameter measuring instrument such as Multisizer III (manufactured by Beckman Coulter, Inc.) and FPIA 3000 (manufactured by Sysmex Corporation).

The average circularity of the additive manufacturing powder represented by the following relation is 0.800 or greater, preferably from 0.940 to 0.980, and more preferably from 0.960 to 0.970. The average circularity is defined as follows:

Average circularity=(a perimeter of circle having same area as a projected image of a particle)/ the (perimeter of the projected image of the particle)×100.

When the average circularity is less than 0.800, the additive manufacturing powder easily agglomerates and also the filling rate thereof in the thin layer when forming a thin layer is insufficient so that voids tend to appear. That is, the object for additive manufacturing tends to have voids.

To the contrary, when the upper limit of the average circularity is suppressed to 0.980 or lower, removing uncured powder present inside becomes easy by air blow after additive manufacturing.

The average circularity can be measured according to known methods using a known circularity measuring instrument such as FPIA 3000 (manufactured by Sysmex Corporation).

There is no specific limit to the method of adjusting the value of Dv/Dn. For example, it can be adjusted by classification.

There is no specific limit to the method of adjusting the value of the average circularity. For example, it can be adjusted by classification.

The additive manufacturing powder of the present disclosure is used to fabricate various molded objects or structures easily and efficiently.

Method of Manufacturing Additive Manufacturing Object and Manufacturing Apparatus of Additive Manufacturing Object The method of manufacturing the additive manufacturing object of the present disclosure includes a process of forming a powder layer for additive manufacturing using the additive manufacturing powder of the present disclosure and other optional processes.

The apparatus of manufacturing the object of additive manufacturing of the present disclosure includes at least a device of forming a powder layer for additive manufacturing using the additive manufacturing powder of the present disclosure and other optional devices.

The method of manufacturing the object of additive manufacturing of the present disclosure can be conducted by a manufacturing apparatus for the object for additive manufacturing. The process of forming a powder layer for additive manufacturing can be conducted by a device forming the powder layer for additive manufacturing. The other optional processes can be executed by the other optional devices.

Process of Forming Powder Layer for Additive Manufacturing and Device for Forming Powder Layer for Additive Manufacturing The process of forming the powder layer for additive manufacturing is to form a powder layer for additive manufacturing having a desired thickness on a substrate using the additive manufacturing powder of the present disclosure.

The device to form the powder layer for additive manufacturing is to form a powder layer for additive manufacturing having a desired thickness on a substrate using the additive manufacturing powder of the present disclosure.

Substrate

There is no specific limit to the substrate the additive manufacturing powder can be placed thereon. It can be selected to a particular application. For example, a board having a surface for the additive manufacturing powder or a base plate illustrated in FIG. 1 of JP-2000-328106-A is suitable. The surface of the substrate, that is, the surface on which the additive manufacturing powder is placed can be smooth, coarse, plane, or curved plane.

Forming Powder Layer for Additive Manufacturing

There is no specific limit to the method of depositing the additive manufacturing powder on a substrate. It can be selected to a particular application. For example, such a thin layer can be formed by a method using a known counter rotation mechanism (counter roller) for use in a selective laser sintering method described in JP-360730-B (JP-2000-505737-A), a method of extending the additive manufacturing powder to a thin layer by a member such as a brush, a roller, and a blade, a method of applying a pressure to the surface of the additive manufacturing powder with a pressing member to extend it to a thin layer, or a method using a known powder laminating device.

Using the counter rotation mechanism (counter roller), the brush, the blade, or the pressing member, a thin layer of the additive manufacturing powder can be formed on a substrate, for example, in the following manner:

In the outer frame (also referred to as "form", "hollow cylinder" "tubular structure", etc.), the additive manufacturing powder is placed by the counter rotation mechanism (counter roller), the brush, the blade, the pressing member, etc. onto the substrate arranged to move up and down slidably in the inside wall of the outer frame. At this point, when a substrate movable up and down in the outer frame is used, the substrate illustrated in FIG. 1 mentioned above is arranged slightly lower than the upper open mouth of the outer frame. That is, while placing the substrate with a layer thickness of the additive manufacturing powder below the open mouth, the additive manufacturing powder is placed on the substrate. Thus, a thin layer of the additive manufacturing powder can be placed on the substrate.

Process of Sintering Powder Layer for Additive Manufacturing and Device for Sintering Powder Layer for Additive Manufacturing In the method of manufacturing an object of additive manufacturing of the present disclosure, it is preferable to include a process of sintering the powder layer for additive manufacturing placed as the thin layer by irradiation of the powder layer with a laser beam or electron beam.

The additive manufacturing powder is cured upon application of such a laser beam or electron beam. On the thin layered cured material (hereinafter referred to as bottom layer for convenience), the additive manufacturing powder is placed again as described above (hereinafter referred to as top layer for convenience). To the powder layer (top layer) for additive manufacturing placed as a thin layer, the layer or the electron beam is applied again to cure the top layer. This curing occurs not only to the top layer but also to the interface with the bottom layer. As a consequence, the cured material (object of additive manufacturing) having a thickness corresponding to about two layers of the top layer and the bottom layer is obtained.

In addition, the additive manufacturing powder can be automatically and easily arranged to form a thin layer on the substrate by a known powder laminating device. A typical powder laminating device has a recoater to laminate the additive manufacturing powder, movable supplying tank to supply the additive manufacturing powder onto the substrate, and a movable layer forming tank to form and laminate a thin layer of the powder.

In the powder laminating device, the surface of the supplying tank can be elevated slightly above the surface of the forming tank by moving up the supplying tank, moving down the forming tank, or both. In addition, the additive manufacturing powder is arranged to form a thin layer using the recoater from the supplying tank and by repeating moving the recoater, the additive manufacturing powder of the thin layer is laminated.

There is no specific limitation to the thickness of the powder layer for additive manufacturing. It can be determined to a particular application. The average thickness of the thin layer is preferably from 3 µm to 200 µm and more preferably from 10 µm to 100 µm. When the average thickness is 3 µm or greater, the time to be taken to obtain an object of additive manufacturing can be shortened and the degree of problem of frame collapse during processing such as sintering and/or handling can be lowered. When the average thickness is 200 µm or less, the dimension accuracy of an object of additive manufacturing is improved. Incidentally, the average thickness can be measured by a known method.

Irradiation of Laser

The laser for use in the laser irradiation has an absorption wavelength range for calcium phosphate. It can be selected to a particular application. For example, $CO_2$ laser, Nd-YAG laser, fiber laser, and semi-conductor laser can be used.

There is no specific limitation to the condition for the laser emission. It can be selected to a particular application. For example, when a small-sized laser is used, it is not possible to melt calcium phosphate, so that it is preferable that an adhesive (polyester) is mixed and melted by laser irradiation to form an object. In such a case, it is preferable to use $CO_2$ laser.

As the irradiation conditions, for example, it is preferable that the laser power is 15 W, the wavelength is 10.6 µm and the beam diameter is about 0.4 mm.

Irradiation of Laser

There is no specific limitation to the electron beams if the beams melt calcium phosphate. It can be selected to a particular application. When the additive manufacturing powder is irradiated with an electron beam, the powder is placed in a vacuum condition. The device for manufacturing the powder layer is the same as above.

There is no specific limitation to the conditions of irradiation of electron beams. It can be determined to a particular application. For example, it is preferable that the laser power is 1,500 W, the beam diameter is about 0.1 mm, and the vacuum degree is about $1.0 \times 10^{-5}$ mbar.

In addition, formed cured materials can be sintered by a known sintering furnace. As a result, the cured materials become an integrated molded object (i.e., object of additive manufacturing).

Other Process and other Device

The other processes include a surface protection treatment process, a coating process, etc.

The other devices include a surface protection treatment device, a coating device, etc.

The surface protection treatment process means the cured material forming process or a process of forming a protection layer on an object formed in the sintering process. By executing the surface protection treatment process, durability is imparted to the surface of the fabricated object to the degree that, for example, the object can be used as is. Specific examples of the protection layer include, but are not limited to, a water-resistant layer, a weather resistant layer, a light resistant layer, a heat insulation layer, and a gloss layer. Specific examples of the surface protection treatment device include, but are not limited to, known surface protection treatment devices such as a spraying device and a coating device.

The coating process executes coating to the object of additive manufacturing. By this coating process, the object is colored in a desired color. Specific examples of the coating device include, but are not limited to, known coating devices using a spray, a roller, a brush.

By the manufacturing method and the manufacturing device of manufacturing an object of additive manufacturing, a complicated solid free-form object can be fabricated easily and efficiently with good dimension accuracy without frame collapse before sintering using the additive manufacturing powder of the present disclosure. Since the thus-obtained object of additive manufacturing has a sufficient strength and excellent dimension accuracy, representing fine roughness and curved planes, the object has aesthetic aspect with high quality and can be suitably used for various purposes.

Having generally described preferred embodiments of this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

The present disclosure is described in detail with reference to Examples and Comparative Examples. However, the present disclosure is not limited to these Examples.

Preparation Example 1

Preparation of Filler 1
Synthesis of α-tricalcium Phosphate (α-TCP)
0.342 mol/dm$^3$ phosphoric acid aqueous solution was sent at a flow speed of 6 mL/min. to a 0.513 mol/dm$^3$ calcium hydroxide suspension liquid stirred at 160 rpm using a paddle available on market followed by adjusting pH around 8.7 by ammonium. Thereafter, subsequent to 72 hour aging in an incubator at 37 degrees C., the resultant was filtered followed by drying to obtain powder. After one hour baking at 800 degrees C., the resultant was ball-mill pulverized by zirconia bead having a diameter of 3 mm.

This ball-mill pulverization was conducted by BM-6 type roller ball mil (manufactured by Glen Creston Ltd.) for 30 minutes followed by screening with 75 μm mesh to obtain fine powder. Thereafter, the fine powder was baked at 1,400 degrees C. for five hours followed by rapid cooling to obtain α-tricalcium phosphate (α-TCP) as Filler 1.

Identification of the crystal phase of the prepared α-tricalcium phosphate was conducted by X-ray powder diffraction instrument (RINT1100, manufactured by Rigaku Corporation) under the following conditions. The crystal phase was found to be α.
Measuring Conditions
X ray tube: Cu
Voltage: 40 kV
Current: 40 mA
Start angle: 3 degree
End angle: 80 degree
Scanning speed: 0.5 degree/min
α-tricalcium phosphate (α-TCP) as [Filler 1] was measured according to the same method as the method for [Additive manufacturing powder 1] described later. The volume average particle diameter Dv was 4.7 μm.

Synthesis of Polyester Resin
The following components are placed in a container equipped with a condenser, a stirrer and a nitrogen introducing tube to conduct a reaction at 230 degrees C. at normal pressure for 8 hours:
Adduct of bisphenol A with 2 mole of ethylene oxide: 67 parts
Adduct of bisphenol A with 3 mole of propylene oxide: 84 parts
Terephthalic acid: 274 parts
Dibutyltin oxide: 2 parts Thereafter, the resultant was caused to conduct 5 hour reaction with a reduced pressure of 10 mm Hg to 15 mm Hg to synthesize a polyester resin. The thus-obtained non-crystalline polyester has an acid value of 17 mg/KOH, a weight average molecular weight Mw of 5,600, and a glass transition temperature of 50 degrees C.

The weight average molecular weight Mw of the synthesized polyester resin is measured by a gel permeation chromatography (GPC) under the following conditions:
Measuring Conditions
Device: GPC-8020 (manufactured by TOSOH CORPORATION)
Column: TSK G2000 HXL and G4000 HXL (manufactured by TOSOH CORPORATION)
Temperature: 40° C.
Solvent: Chloroform
Flow speed: 1.0 mL/minute
1 mL of the sample having a concentration of 0.5 percent by weight was infused into the column and the weight average molecular weight Mw was calculated by using the molecular weight calibration curve obtained based on a simple dispersion polystyrene standard sample from the molecular weight distribution of the polymer measured under the conditions specified above. Incidentally, in the analysis, the polyester resin was dissolved in chloroform at 0.15 percent by weight followed by 0.2 μm filter. The filtrate was used as the sample.

In addition, the glass transition temperature Tg of the synthesized polyester resin was measured under the following conditions using TA-60WS and DSC-60, both manufactured by Shimadzu Corporation

| Measuring Conditions | |
| --- | --- |
| Sample container: | Aluminum sample pan (with a lid) |
| Sample amount: | 5 mg |
| Reference: | Aluminum sample pan (alumina 10 mg) |
| Atmosphere: | nitrogen (flow amount: 50 ml/min) |
| Temperature Conditions | |
| Starting Temperature: | 20 degrees C. |
| Heating speed: | 10 degrees C./min |
| Ending temperature: | 150 degrees C. |
| Holding time: | None |
| Cooling speed: | −10 degrees C./min |
| Ending temperature: | 20 degrees C. |
| Holding time: | None |
| Heating speed: | 10 degrees C./min |
| Ending temperature: | 150 degrees C. |

The measuring results were analyzed by using data analysis software (TA-60, version 1.52, manufactured by Shimadzu Corporation). To be specific, by assigning a range of from +5 degrees C. to −5 degrees C. relative to the maximum peak on the lowest temperature side of DrDSC curve representing the DSC differential curve in the second temperature rise, the peak temperature is obtained using a peak analysis feature of the analysis software. Next, in the range of from +5 degrees C. to −5 degrees C. relative to the peak temperature of the DSC curve, the maximum endothermic peak of the DSC curve using the peak analysis feature of the analysis software. The temperature shown here corresponds to the glass transition temperature Tg of the polyester resin.

Preparation of Powder Material for Additive Manufacturing
40 parts by weight of [Filler 1] and 60 parts of the polyester resin were placed in a twin-shaft kneader (PCM-43, manufactured by Ikegai Corp.). [Powder material for additive manufacturing] was obtained by mixing and kneading at a rotation speed of 200 rpm and the mixing and kneading temperature of 190 degrees C. The supplying speed of the raw materials into the kneader was 10 kg/h and the average detention time was one minute.

Preparation of Powder Phase for Additive Manufacturing 100 parts by weight of [Powder material for additive manufacturing] (60 parts of polyester resin+40 parts of [Filler 1]) and 130 parts of ethyl acetate were charged into a beaker followed by stirring for dissolution. Next, using a bead mill (ULTRA VISCO MILL, manufactured by IMEX Co., Ltd.), [Solution or liquid dispersion of material] was prepared under the conditions of a liquid sending speed of 1 kg/h, a disk perimeter speed of 6 m/s, 80 percent by volume filling of 0.5 mm zirconia beads, and 3 passes.

Preparation of Styrene Acrylic Resin Particulate

The following recipe was placed in a reaction container equipped with a stirrer and a thermometer and stirred at 400 rpm for 15 minutes to obtain a white emulsion:

| | |
|---|---|
| Water: | 683 parts |
| Sodium salt of sulfuric acid ester of an adduct of methacrylic acid with ethyleneoxide (EREMINORRS-30, manufactured by Sanyo Chemical Industries, Ltd.): | 16 parts |
| Styrene: | 83 parts |
| Methacrylic acid: | 83 parts |
| Butyl acrylate: | 110 parts |
| Ammonium persulfate: | 1 part. |

The system was heated to 75 degrees C. to conduct reaction for five hours. Furthermore, 30 parts of 1 percent ammonium persulfate aqueous solution was added followed by aging at 75 degrees C. for five hours to obtain an aqueous liquid dispersion [Liquid dispersion of styrene acrylic resin particulate A] of a vinyl resin (copolymer of styrene-methacrylic acid-butyl acrylate-sodium salt of sulfuric acid ester of an adduct of methacrylic acid with ethylene oxide). [Liquid dispersion of styrene acrylic resin particulate A] had a volume average particle diameter (measured by LA-920, manufactured by Horiba Corporation) of 44 nm, an acid value of 180 mgKOH/g, a weight average molecular weight Mw of 500,000, and a Tg of 62 degrees C.

Thereafter, [Liquid dispersion of styrene acrylic resin particulate B] was synthesized in the same manner as in [Liquid dispersion of styrene acrylic resin particulate A] except that the stirring speed was changed to 600 rpm. [Liquid dispersion of styrene acrylic resin particulate B] had a volume average particle diameter (measured by LA-920, manufactured by Horiba Corporation) of 20 nm, an acid value of 180 mgKOH/g, a weight average molecular weight Mw of 500,000, and a Tg of 62 degrees C.

Thereafter, [Liquid dispersion of styrene acrylic resin particulate C] was synthesized in the same manner as in [Liquid dispersion of styrene acrylic resin particulate A] except that the stirring speed was changed to 300 rpm. [Liquid dispersion of styrene acrylic resin particulate C] had a volume average particle diameter (measured by LA-920, manufactured by Horiba Corporation) of 60 nm, an acid value of 180 mgKOH/g, a weight average molecular weight Mw of 500,000, and a Tg of 62 degrees C.

Evaluation of Styrene Acrylic Resin Particulate

The styrene-acrylic resins as the second binder resin were added to a screw vial (30 mL, manufactured by AS ONE Corporation.) in such a manner that each of the resins reached 20 mL from the bottom followed by charging of 10 mL of ethyl acetate with pipette. After the resultant was left still for 24 hours, it was phase-separated in such a manner that an emulsion of white resin particulates was to the bottom and ethylacetate to the top. Swelling to ethylacetate was evaluated by observing the height of the white resin particulate emulsion from the bottom of the screw vial. A higher height reading means higher swelling. The degree of swelling was evaluated by observing the height of the resin particulate emulsion as follows: "Swelling" means the subject to be evaluated as A, B, or C.

| Evaluation Criteria of Swelling | |
|---|---|
| A: 21 mm or greater | Swelling |
| B: 20 mm to less than 21 mm | Insufficiently swelling |
| C: Less than 20 mm | No swelling |

Evaluation results of swelling of the styrene-acrylic resin particulates and compatibility with the first binder resin (here, polyester resin) are shown in Table 1.

TABLE 1

| | Swelling | Compatibility with first binder resin | Volume average particle diameter |
|---|---|---|---|
| Liquid dispersion of styrene acrylic resin particulate A | A | Non-compatible | 44 nm |
| Liquid dispersion of styrene acrylic resin particulate B | A | Non-compatible | 20 nm |
| Liquid dispersion of styrene acrylic resin particulate C | A | Non-compatible | 60 nm |

Manufacturing of Additive Manufacturing Powder 1

Preparation of Aqueous Medium Phase 660 parts of water, 25 parts of [Liquid dispersion of styrene acrylic resin particulate A], 25 parts of 48.5 percent by weight aqueous solution of sodium dodecyldiphenyl etherdisulfonate (EREMINOR MON-7, manufactured by Sanyo Chemical Industries, Ltd.), and 60 parts of ethyl acetate were mixed and stirred to obtain milk white liquid (aqueous phase).

Preparation of Emulsion and/or Liquid Dispersion 150 parts of the aqueous medium phase was placed in a container and stirred at 12,000 rpm by a TK type HOMO-MIXER (manufactured by PRIMIX Corporation). 100 parts of [Solution or liquid dispersion of material] was added thereto followed by mixing for 10 minutes to prepare an emulsion and/or liquid dispersion (emulsion slurry).

Removal of Organic Solvent 100 parts of the emulsion slurry was placed in a flask equipped with a pipe for degassing, a stirrer, and a thermometer and stirred at a stirring speed of 20 m/min to remove the solvent at 30 degrees C. with a reduced pressure for 12 hours to obtain a solvent-removed slurry.

Washing

After all of the solvent-removed slurry was filtered with a reduced pressure, 300 parts of deionized water was added to the filtered cake and mixed and re-dispersed by a TK HOMOMIXER at 12,000 rpm for 10 minutes followed by filtration. 300 parts of deionized water was added to the thus-obtained filtered cake and the resultant was mixed by a TK HOMOMIXER at 12,000 rpm for 10 minutes followed by filtration, which was repeated three times. The resultant having a conductivity of the re-dispersed slurry ranging from 0.1 µS/cm to 10 µS/cm was defined as washed slurry.

Drying

The obtained filtered cake was dried by a circulation drier at 45 degrees C. for 48 hours. The dried cake was sieved using a screen having an opening diameter of 75 µm to obtain [Additive manufacturing powder 1]. [Additive manufacturing powder 1] had a core-shell type particle having a shell on the surface of a core particle.

Measuring of Additive Manufacturing Powder 1

The volume average particle diameter Dv and the number average particle diameter Dn of the obtained [Additive manufacturing powder 1] were measured by a particle size measuring instrument (MULTISIZER III, manufactured by BECKMAN COULTER INC.) with an aperture diameter of 100 μm and the measuring results were analyzed by an analysis software (BECKMAN COULTER MULTISIZER 3 VERSION 3.51). To be specific, 0.5 ml of 10 percent by weight surfactant (alkylbenzene sulfonate, NEOGEN SC-A, manufactured by Daiichi Kogyo Co., Ltd.) was charged into a glass beaker (100 ml). 0.5 g of [Additive manufacturing powder 1] was added into the beaker and stirred by a microspatula. Thereafter, 80 ml of deionized water was added to the mixture. The thus-obtained liquid dispersion was subject to dispersion treatment for ten minutes using an ultrasonic wave dispersion device (W-113MK-II, manufactured by Honda Electronics). The liquid dispersion was measured by using the MULTISIZER III using ISOTON® III (manufactured by BECKMAN COULTER INC.) as the measuring solution. The sample liquid dispersion of [Additive manufacturing powder 1] was dripped such that the concentration indicated by the measuring device was from 6 percent to 10 percent. In this measuring method, it is suitable to keep the concentration in the range mentioned above in terms of measuring reproducibility. The measured particle diameter can be obtained without an error when the concentration is within that range.

The particle size distribution Dv/Dn was obtained from the thus-obtained volume average particle diameter Dv and the number average particle diameter Dn.

The average circularity of the obtained [Additive manufacturing powder 1] is defined as follows:

Average circularity=(a perimeter of a circle having same area as a projected image of a particle)/ the (perimeter of the projected image of the particle)×100.

The average circularity is measured and calculated by measuring the particles by a flow type particle image analyzer (FPIA-2100, manufactured by Sysmex Corporation) followed by analysis using an analysis software (FPIA-2100 Data Processing Program For FPIA Version 00-10).

To be specific, 0.1 ml to 0.5 ml of 10 percent by weight surfactant (alkylbenzene sulfonate, NEOGEN SC-A, manufactured by Daiichi Kogyo Co., Ltd.) was charged into a glass beaker (100 ml). 0.1 g to 0.5 g of [Additive manufacturing powder 1] was added into the beaker and stirred by a microspatula. Thereafter, 80 ml of deionized water was added to the mixture. The thus-obtained liquid dispersion was subject to dispersion treatment for three minutes by an ultrasonic wave dispersion device (manufactured by Honda Electronics). The form and distribution of [Additive manufacturing powder 1] were measured by measuring the liquid dispersion by FPIA-2100 until the concentration was 5,000 particles/μl to 15,000 particles/μl.

In this measuring method, it is suitable to make the concentration of the liquid dispersion from 5,000 particles/μl to 15,000 particles/μl in terms of the measuring reproducibility of the average circularity. To obtain the concentration of the liquid dispersion, it is suitable to change the conditions of the liquid dispersion, that is, the amount of the surfactant to be added and the amount of [Additive manufacturing powder 1] are changed. The suitable amount of the surfactant varies depending on the hydrophobicity of [Additive manufacturing powder 1] as in the measuring of the particle diameter thereof. If an excessively large amount is added, the noise ascribable to bubbles tends to occur. If an excessively small amount is added. [Additive manufacturing powder 1] tends to be insufficiently wet, which leads to insufficient dispersion.

In addition, the addition amount of [Additive manufacturing powder 1] depends on the particle diameter. In a case of a small particle diameter, the amount is required to increase and, a large particle diameter, decrease. When the particle diameter of [Additive manufacturing powder 1] is from 3 μm to 7 μm, the addition amount of [Additive manufacturing powder 1] is 0.1 g to 0.5 g, thereby adjusting the concentration of the liquid dispersion to be 5,000 particles/μl to 15,000 particles/μl.

The measuring results are shown in Table 2.

Preparation of Filler 2

Synthesis of α-tricalcium Phosphate (β-TCP)

0.342 mol/dm$^3$ phosphoric acid aqueous solution was sent at 6 mL/min. to a suspension liquid of 0.513 mol/dm$^3$ calcium hydroxide stirred at 160 rpm by a paddle available on market followed by stabilizing the pH around 8.7 by ammonium. Thereafter, subsequent to 72 hour aging in an incubator at 37 degrees C., the resultant was filtered followed by drying to obtain powder. After one hour baking at 800 degrees C., the resultant was (ball-mill) pulverized by zirconia bead having a diameter of 3 mm.

This ball-mill pulverization was conducted by BM-6 type roller ball mil (manufactured by Glen Creston Ltd.) for 30 minutes followed by screening with 75 μm mesh to obtain fine powder. Thereafter, the fine powder was baked at 1,100 degrees C. for five hours followed by rapid cooling to obtain β-tricalcium phosphate (β-TCP) as [Filler 2].

β-TCP as the thus-obtained [Filler 2] was measured in the same manner as in Preparation of [Filler 1]. The volume average particle diameter Dv was 5.0 μm.

Preparation of Filler 3

Synthesis of Octacalcium Phosphate (OCP)

0.342 mol/dm$^3$ phosphoric acid aqueous solution was sent at 6 mL/min. to a suspension liquid of 0.455 mol/dm$^3$ calcium hydroxide stirred at 160 rpm using a paddle available on market followed by adjusting pH around 8.7 by ammonium. Thereafter, subsequent to 72 hour aging in an incubator at 37 degrees C., the resultant was filtered followed by drying to obtain powder. After one hour baking at 800 degrees C., the resultant was ball-mill pulverized by zirconia bead having a diameter of 3 mm. This ball-mill pulverization was conducted by BM-6 type roller ball mil (manufactured by Glen Creston Ltd.) for 30 minutes followed by screening with 75 μm mesh to obtain fine powder. Thereafter, the fine powder was baked at 1,100 degrees C. for five hours followed by rapid cooling to obtain octacalcium phosphate (OCP) as [Filler 3].

OCP as the thus-obtained [Filler 3] was measured in the same manner as in Preparation of [Filler 1]. The volume average particle diameter Dv was 7.0 μm.

Preparation of Filler 4

Synthesis of Hydroxyapatite (HAp)

0.300 mol/dm$^3$ phosphoric acid aqueous solution was sent at 6 mL/min. to a suspension liquid of 0.500 mol/dm$^3$ calcium hydroxide stirred at 160 rpm using a paddle available on market followed by adjusting pH around 8.7 by ammonium. Thereafter, subsequent to 72 hour aging in an incubator at 37 degrees C., the resultant was filtered followed by drying to obtain powder. After one hour baking at 800 degrees C., the resultant was (ball-mill) pulverized by zirconia bead having a diameter of 3 mm.

This ball-mill pulverization was conducted by BM-6 type roller ball mil (manufactured by Glen Creston Ltd.) for 30 minutes followed by screening with 75 µm mesh to obtain fine powder. Thereafter, the fine powder was baked at 1,000 degrees C. for five hours to obtain hydroxyapatite (HAp) as [Filler 4].

HAp as the thus-obtained [Filler 4] was measured in the same manner as in Preparation of [Filler 1]. The volume average particle diameter Dv was 5.0 µm.

Example 1

With regard to [Additive manufacturing powder 1], [Additive manufacturing object 1] was fabricated using an outer frame.

1. Using a powder laminating device (jig for powder, manufactured by Niigata Co., Ltd.), [Additive manufacturing powder 1] was transferred from a supplying tank to a molding tank and a thin layer of [Additive manufacturing powder 1] having an average thickness of 100 µm was formed on a substrate.

2. Thereafter, the surface of the formed thin layer of [Additive manufacturing Powder 1] was irradiated with $CO_2$ laser (LP-400, manufactured by Panasonic Industrial Devices SUNX Co., Ltd.) to sinter [Additive manufacturing powder 1] to sinter calcium phosphate.

3. Next, the operations 1 and 2 were repeated to sequentially laminate the thin layer of [Additive manufacturing powder 1] until the total average thickness was 3 mm, thereby manufacturing [Additive manufacturing object 1].

Extra additive manufacturing powder was removed by air blow for the obtained [Additive manufacturing object 1]. No frame collapse occurred. The obtained [Additive manufacturing object 1] had a high level of strength and excellent dimension accuracy. The obtained [Additive manufacturing object 1] was evaluated about strength and dimension accuracy according to the following criteria. The results are shown in Table 2.

Strength (Hardness)

Evaluation was conducted according to the following criteria.

A: No additive manufacturing powder cured sufficiently yet and the additive manufacturing object not be able to be taken out of the outer frame. If taken out, a predetermined form was not sustained.

B: Only extra additive manufacturing powder was removed when the additive manufacturing object was air-blown. The object kept its form.

Dimension Accuracy

Evaluation was conducted according to the following criteria.

A: Surface of obtained additive manufacturing object distorted. Additive manufacturing powder found to be locally present by observation of surface by SEM B: State of surface of obtained additive manufacturing object was good with slight warp C: Obtained additive manufacturing object having smooth and beautiful surface with no warp 4. The [Additive manufacturing object 1] obtained in 3 was sintered in vacuum condition at 1,300 degrees C.

This [Additive manufacturing object 1] was a perfectly integrated structure of calcium phosphate and did not break when slummed down on a hard floor.

Example 2

[Additive manufacturing object 2] was manufactured in the same manner as in Example 1 except that α-TCP as [Filler 1] was changed to β-TCP as [Filler 2]. The obtained [Additive manufacturing object 2] was evaluated in the same manner as in Example 1. The results are shown in Table 2.

Example 3

[Additive manufacturing object 3] was manufactured in the same manner as in Example 1 except that α-TCP as [Filler 1] was changed to OCP as [Filler 3]. The obtained [Additive manufacturing object 3] was evaluated in the same manner as in Example 1. The results are shown in Table 2.

Example 4

[Additive manufacturing object 4] was manufactured in the same manner as in Example 1 except that α-TCP as [Filler 1] was changed to HAp as [Filler 4]. The obtained [Additive manufacturing object 4] was evaluated in the same manner as in Example 1. The results are shown in Table 2.

Example 5

[Additive manufacturing object 5] was manufactured in the same manner as in Example 1 except that α-TCP as [Filler 1] was changed to carbon nano-tube (NT-7K, manufactured by HODOGAYA CHEMICAL CO., LTD.). The obtained [Additive manufacturing object 5] was evaluated in the same manner as in Example 1. The results are shown in Table 2.

Example 6

[Additive manufacturing object 6] was manufactured in the same manner as in Example 1 except that α-TCP as [Filler 1] was changed to graphene. The obtained [Additive manufacturing object 6] was evaluated in the same manner as in Example 1. The results are shown in Table 2.

Example 7

[Additive manufacturing object 7] was manufactured in the same manner as in Example 1 except that α-TCP as [Filler 1] was changed to fullerene. The obtained [Additive manufacturing object 7] was evaluated in the same manner as in Example 1. The results are shown in Table 2.

Example 8

[Additive manufacturing object 8] was manufactured in the same manner as in Example 1 except that the volume average particle diameter Dv of α-TCP as Filler 1 was changed to 4.0 µm. The obtained [Additive manufacturing object 8] was evaluated in the same manner as in Example 1. The results are shown in Table 2.

Example 9

[Additive manufacturing object 9] was manufactured in the same manner as in Example 1 except that the volume average particle diameter Dv of [Additive manufacturing powder 1] was changed to 10.0 µm. The obtained [Additive manufacturing object 9] was evaluated in the same manner as in Example 1. The results are shown in Table 2.

Example 10

[Additive manufacturing object 10] was manufactured in the same manner as in Example 1 except that the particle size distribution Dv/Dn of [Additive manufacturing powder 1] was changed to 1.25. The obtained [Additive manufacturing object 10] was evaluated in the same manner as in Example 1. The results are shown in Table 2.

Example 11

[Additive manufacturing object 11] was manufactured in the same manner as in Example 1 except that the average circularity of [Additive manufacturing powder 1] was changed to 0.940 by classification. The obtained [Additive manufacturing object 11] was evaluated in the same manner as in Example 1. The results are shown in Table 2.

Example 12

[Additive manufacturing object 12] was manufactured in the same manner as in Example 1 except that the average circularity of [Additive manufacturing powder 1] was changed to 0.980 by classification. The obtained [Additive manufacturing object 12] was evaluated in the same manner as in Example 1. The results are shown in Table 2.

Example 13

[Additive manufacturing object 13] was manufactured in the same manner as in Example 1 except that the glass transition temperature Tg of the polyester resin was changed to 30 degrees C. The obtained [Additive manufacturing object 13] was evaluated in the same manner as in Example 1. The results are shown in Table 2.

Example 14

[Additive manufacturing object 14] was manufactured in the same manner as in Example 1 except that the glass transition temperature Tg of the polyester resin was changed to 80 degrees C. The obtained [Additive manufacturing object 14] was evaluated in the same manner as in Example 1. The results are shown in Table 2.

Example 15

[Additive manufacturing object 15] was manufactured in the same manner as in Example 1 except that the acid value of the polyester resin was changed to 10 mgKOH/g. The obtained [Additive manufacturing object 15] was evaluated in the same manner as in Example 1. The results are shown in Table 2.

Example 16

[Additive manufacturing object 16] was manufactured in the same manner as in Example 1 except that the acid value of the polyester resin was changed to 30 mgKOH/g. The obtained [Additive manufacturing object 16] was evaluated in the same manner as in Example 1. The results are shown in Table 2.

Example 17

[Additive manufacturing object 17] was manufactured in the same manner as in Example 1 except that the weight average molecular weight Mw of the polyester resin was changed to 4,000. The obtained [Additive manufacturing object 17] was evaluated in the same manner as in Example 1. The results are shown in Table 2.

Example 18

[Additive manufacturing object 18] was manufactured in the same manner as in Example 1 except that the weight average molecular weight Mw of the polyester resin was changed to 20,000. The obtained [Additive manufacturing object 18] was evaluated in the same manner as in Example 1. The results are shown in Table 2.

Example 19

[Additive manufacturing object 19] was manufactured in the same manner as in Example 1 except that the acid value of the styrene-acrylic resin was changed to 150 mgKOH/g. The obtained [Additive manufacturing object 19] was evaluated in the same manner as in Example 1. The results are shown in Table 2.

Example 20

[Additive manufacturing object 20] was manufactured in the same manner as in Example 1 except that the acid value of the styrene-acrylic resin was changed to 250 mgKOH/g. The obtained [Additive manufacturing object 20] was evaluated in the same manner as in Example 1. The results are shown in Table 2.

Example 21

[Additive manufacturing object 21] was manufactured in the same manner as in Example 1 except that, in Manufacturing of [Additive Manufacturing Powder 1], [Liquid dispersion of styrene acrylic resin particulate A] having a volume average particle diameter Dv of 44 nm was changed to [Liquid dispersion of styrene acrylic resin particulate B] having a volume average particle diameter Dv of 20 nm. The obtained [Additive manufacturing object 21] was evaluated in the same manner as in Example 1. The results are shown in Table 2.

Example 22

[Additive manufacturing object 22] was manufactured in the same manner as in Example 1 except that, in Manufacturing of [Additive Manufacturing Powder 1], [Liquid dispersion of styrene acrylic resin particulate A] having a volume average particle diameter Dv of 44 nm was changed to [Liquid dispersion of styrene acrylic resin particulate C] having a volume average particle diameter Dv of 60 nm. The obtained [Additive manufacturing object 21] was evaluated in the same manner as in Example 1. The results are shown in Table 2.

Example 23

[Additive manufacturing object 23] was manufactured in the same manner as in Example 1 except that the weight average molecular weight Mw of the styrene-acrylic resin was changed to 200,000. The obtained [Additive manufacturing object 23] was evaluated in the same manner as in Example 1. The results are shown in Table 2.

Example 24

[Additive manufacturing object 24] was manufactured in the same manner as in Example 1 except that the weight average molecular weight Mw of the styrene-acrylic resin was changed to 800,000. The obtained [Additive manufacturing object 24] was evaluated in the same manner as in Example 1. The results are shown in Table 2.

Example 25

[Additive manufacturing object 25] was manufactured in the same manner as in Example 1 except that the glass transition temperature Tg of the styrene-acrylic resin was changed to 30 degrees C. The obtained [Additive manufacturing object 25] was evaluated in the same manner as in Example 1. The results are shown in Table 2.

Example 26

[Additive manufacturing object 26] was manufactured in the same manner as in Example 1 except that the glass transition temperature Tg of the styrene-acrylic resin was changed to 80 degrees C. The obtained [Additive manufacturing object 26] was evaluated in the same manner as in Example 1. The results are shown in Table 2.

Example 27

[Additive manufacturing object 27] was manufactured in the same manner as in Example 1 except that sintering by the laser beam was changed to by electron beam melting (EBM) under the following conditions. EBM was conducted by self-built electron beam irradiator. The irradiation condition: output power: 1,500 W, beam diameter: 0.1 mm, and degree of vacuum: $1.0 \times 10^{-5}$ mbar.

1. Using a powder laminating device (jig for powder, manufactured by Niigata Co., Ltd.), [Additive manufacturing powder 1] was transferred from a supplying tank to a molding tank and a thin layer of [Additive manufacturing powder 1] having an average thickness of 100 μm was formed on a substrate.

2. Thereafter, the surface of the formed thin layer of [Additive manufacturing powder 1] was irradiated with self-built electron beam to sinter [Additive manufacturing powder 1] to sinter calcium phosphate.

3. Next, the operations 1 and 2 were repeated to sequentially laminate the thin layer of [Additive manufacturing powder 1] until the total average thickness was 3 mm, thereby manufacturing [Additive manufacturing object 27].

Extra additive manufacturing powder was removed by air blow for the obtained additive manufacturing object 27. No frame collapse occurred. The obtained [Additive manufacturing object 27] had a high level of strength and excellent dimension accuracy. The obtained [Additive manufacturing object 27] was evaluated in the same manner as in Example 1. The results are shown in Table 2.

Example 28

[Additive manufacturing object 28] was manufactured in the same manner as in Example 1 except that the average circularity of [Additive manufacturing powder 1] was changed to 0.857 by classification. The obtained [Additive manufacturing object 28] was evaluated in the same manner as in Example 1. The results are shown in Table 2.

Example 29

[Additive manufacturing object 29] was manufactured in the same manner as in Example 1 except that the particle size distribution Dv/Dn of [Additive manufacturing powder 1] was changed to 1.42. The obtained [Additive manufacturing object 29] was evaluated in the same manner as in Example 1. The results are shown in Table 2.

Example 30

[Additive manufacturing object 30] was manufactured in the same manner as in Example 1 except that the addition amount of the filler was changed to 30 parts. The obtained [Additive manufacturing object 30] was evaluated in the same manner as in Example 1. The results are shown in Table 2.

Example 31

[Additive manufacturing object 31] was manufactured in the same manner as in Example 1 except that the relation A/B, where A represents the volume average particle diameter of the filler and B represents the volume average particle diameter of the additive manufacturing powder containing the filler, was changed to 0.79. The obtained [Additive manufacturing object 31] was evaluated in the same manner as in Example 1. The results are shown in Table 2.

Comparative Example 1

Additive manufacturing object 32 was manufactured in the same manner as in Example 1 except that the first binder resin of the polyester resin was changed to acrylic resin. The obtained [Additive manufacturing object 32] was evaluated in the same manner as in Example 1. The results are shown in Table 2.

In Comparative Example 1, particles for additive manufacturing powder were not formed so that no core-shell type particles were obtained.

Comparative Example 2

[Additive manufacturing object 33] was manufactured in the same manner as in Example 1 except that the second binder resin of the styrene-acrylic resin was changed to an acrylic resin. The obtained [Additive manufacturing object 33] was evaluated in the same manner as in Example 1. The results are shown in Table 2.

In Comparative Example 2, particles for additive manufacturing powder were not formed so that no core-shell type particles were obtained.

Comparative Example 3

[Additive manufacturing object 34] was manufactured in the same manner as in Example 1 except that no first binder resin of the polyester resin was used. The obtained [Additive manufacturing object 34] was evaluated in the same manner as in Example 1. The results are shown in Table 2.

In Comparative Example 3, particles for additive manufacturing powder were not formed so that no core-shell type particles were obtained.

Comparative Example 4

[Additive manufacturing object 35] was manufactured in the same manner as in Example 1 except that no second binder resin of the styrene-acrylic resin was used. The obtained [Additive manufacturing object 35] was evaluated in the same manner as in Example 1. The results are shown in Table 2.

In Comparative Example 4, particles for additive manufacturing powder were not formed so that no core-shell type particles were obtained.

Comparative Example 5

[Additive manufacturing object 36] was manufactured in the same manner as in Example 1 except that additive manufacturing powder obtained by melt-kneading the first binder resin of the polyester resin and α-tricalcium phosphate as [Filler 1] was used. The obtained [Additive manufacturing object 36] was evaluated in the same manner as in Example 1. The results are shown in Table 2.

Comparative Example 6

[Additive manufacturing object 37] was manufactured in the same manner as in Example 1 except that, in the particle forming process, polyester resin particles prepared by using no α-tricalcium phosphate as [Filler 1] and additive manufacturing powder obtained by mixing with α-tricalcium phosphorate were used. The obtained [Additive manufacturing object 37] was evaluated in the same manner as in Example 1. The results are shown in Table 2.

The formulation and evaluation results of Examples and Comparative Example are shown in Table 2.

In Table 2, CNT represents carbon nano-tube, PES represents polyester resin, Ac represents acrylic resin, and St/Ac represents styrene-acrylic resin. In addition, the addition amount of the filler is to the additive manufacturing powder.

TABLE 2

| | | | Filler | | First binder resin | | | |
|---|---|---|---|---|---|---|---|---|
| | Fabrication system | Particle formation | Kind | Addition amount (% by weight) | Kind of resin | Tg (degrees C.) | Acid value (mgKOH/g) | Mw |
| Example 1 | Laser | Granulation | α-TCP | 40 | PES | 50 | 17 | 5,600 |
| Example 2 | Laser | Granulation | β-TCP | 40 | PES | 50 | 17 | 5,600 |
| Example 3 | Laser | Granulation | OCP | 40 | PES | 50 | 17 | 5,600 |
| Example 4 | Laser | Granulation | HAp | 40 | PES | 50 | 17 | 5,600 |
| Example 5 | Laser | Granulation | CNT | 40 | PES | 50 | 17 | 5,600 |
| Example 6 | Laser | Granulation | Graphene | 40 | PES | 50 | 17 | 5,600 |
| Example 7 | Laser | Granulation | Fullerene | 40 | PES | 50 | 17 | 5,600 |
| Example 8 | Laser | Granulation | α-TCP | 40 | PES | 50 | 17 | 5,600 |
| Example 9 | Laser | Granulation | α-TCP | 40 | PES | 50 | 17 | 5,600 |
| Example 10 | Laser | Granulation | α-TCP | 40 | PES | 50 | 17 | 5,600 |
| Example 11 | Laser | Granulation | α-TCP | 40 | PES | 50 | 17 | 5,600 |
| Example 12 | Laser | Granulation | α-TCP | 40 | PES | 50 | 17 | 5,600 |
| Example 13 | Laser | Granulation | α-TCP | 40 | PES | 30 | 19 | 6,200 |
| Example 14 | Laser | Granulation | α-TCP | 40 | PES | 80 | 23 | 5,400 |
| Example 15 | Laser | Granulation | α-TCP | 40 | PES | 67 | 10 | 8,200 |
| Example 16 | Laser | Granulation | α-TCP | 40 | PES | 59 | 30 | 6,900 |
| Example 17 | Laser | Granulation | α-TCP | 40 | PES | 55 | 27 | 4,000 |
| Example 18 | Laser | Granulation | α-TCP | 40 | PES | 76 | 15 | 20,000 |
| Example 19 | Laser | Granulation | α-TCP | 40 | PES | 50 | 17 | 5,600 |
| Example 20 | Laser | Granulation | α-TCP | 40 | PES | 50 | 17 | 5,600 |
| Example 21 | Laser | Granulation | α-TCP | 40 | PES | 50 | 17 | 5,600 |
| Example 22 | Laser | Granulation | α-TCP | 40 | PES | 50 | 17 | 5,600 |
| Example 23 | Laser | Granulation | α-TCP | 40 | PES | 50 | 17 | 5,600 |
| Example 24 | Laser | Granulation | α-TCP | 40 | PES | 50 | 17 | 5,600 |
| Example 25 | Laser | Granulation | α-TCP | 40 | PES | 50 | 17 | 5,600 |
| Example 26 | Laser | Granulation | α-TCP | 40 | PES | 50 | 17 | 5,600 |
| Example 27 | Electron beam | Granulation | α-TCP | 40 | PES | 50 | 17 | 5,600 |
| Example 28 | Laser | Granulation | α-TCP | 40 | PES | 50 | 17 | 5,600 |
| Example 29 | Laser | Granulation | α-TCP | 40 | PES | 50 | 17 | 5,600 |
| Example 30 | Laser | Granulation | α-TCP | 30 | PES | 50 | 17 | 5,600 |
| Example 31 | Laser | Granulation | α-TCP | 40 | PES | 50 | 17 | 5,600 |
| Comparative Example 1 | Laser | Granulation | α-TCP | 40 | Ac | 66 | 28 | 11,000 |
| Comparative Example 2 | Laser | Granulation | α-TCP | 40 | PES | 50 | 17 | 5,600 |
| Comparative Example 3 | Laser | Granulation | α-TCP | 40 | None | — | — | — |
| Comparative Example 4 | Laser | Granulation | α-TCP | 40 | PES | 50 | 17 | 5,600 |
| Comparative Example 5 | Laser | Melt-kneading | α-TCP | 40 | PES | 50 | 17 | 5,600 |
| Comparative Example 6 | Laser | Mixing powder | α-TCP | 40 | PES | 50 | 17 | 5,600 |

TABLE 2-continued

| | Second binder resin | | | | |
|---|---|---|---|---|---|
| | Kind of resin | Tg (degrees C.) | Acid value (mgKOH/g) | Mw | Particle diameter (nm) |
| Example 1 | St/Ac | 62 | 180 | 500,000 | 44 |
| Example 2 | St/Ac | 62 | 180 | 500,000 | 44 |
| Example 3 | St/Ac | 62 | 180 | 500,000 | 44 |
| Example 4 | St/Ac | 62 | 180 | 500,000 | 44 |
| Example 5 | St/Ac | 62 | 180 | 500,000 | 44 |
| Example 6 | St/Ac | 62 | 180 | 500,000 | 44 |
| Example 7 | St/Ac | 62 | 180 | 500,000 | 44 |
| Example 8 | St/Ac | 62 | 180 | 500,000 | 44 |
| Example 9 | St/Ac | 62 | 180 | 500,000 | 44 |
| Example 10 | St/Ac | 62 | 180 | 500,000 | 44 |
| Example 11 | St/Ac | 62 | 180 | 500,000 | 44 |
| Example 12 | St/Ac | 62 | 180 | 500,000 | 44 |
| Example 13 | St/Ac | 62 | 180 | 500,000 | 44 |
| Example 14 | St/Ac | 62 | 180 | 500,000 | 44 |
| Example 15 | St/Ac | 62 | 180 | 500,000 | 44 |
| Example 16 | St/Ac | 62 | 180 | 500,000 | 44 |
| Example 17 | St/Ac | 62 | 180 | 500,000 | 44 |
| Example 18 | St/Ac | 62 | 180 | 500,000 | 44 |
| Example 19 | St/Ac | 50 | 150 | 620,000 | 38 |
| Example 20 | St/Ac | 58 | 250 | 430,000 | 52 |
| Example 21 | St/Ac | 64 | 221 | 480,000 | 20 |
| Example 22 | St/Ac | 68 | 163 | 680,000 | 60 |
| Example 23 | St/Ac | 36 | 237 | 200,000 | 47 |
| Example 24 | St/Ac | 77 | 155 | 800,000 | 55 |
| Example 25 | St/Ac | 30 | 204 | 230,000 | 31 |
| Example 26 | St/Ac | 80 | 169 | 770,000 | 36 |
| Example 27 | St/Ac | 62 | 180 | 500,000 | 44 |
| Example 28 | St/Ac | 62 | 180 | 500,000 | 44 |
| Example 29 | St/Ac | 62 | 180 | 500,000 | 44 |
| Example 30 | St/Ac | 62 | 180 | 500,000 | 44 |
| Example 31 | St/Ac | 62 | 180 | 500,000 | 44 |
| Comparative Example 1 | St/Ac | 62 | 180 | 500,000 | 44 |
| Comparative Example 2 | Ac | 77 | 192 | 440,000 | 61 |
| Comparative Example 3 | St/Ac | 62 | 180 | 500,000 | 44 |
| Comparative Example 4 | None | — | — | — | — |
| Comparative Example 5 | None | — | — | — | — |
| Comparative Example 6 | St/Ac | 62 | 180 | 500,000 | 44 |

| | Additive manufacturing powder | | | | Additive manufacturing object | |
|---|---|---|---|---|---|---|
| | Particle diameter (μm) | A/B | Particle size distribution | Circularity | Strength | Dimension Accuracy |
| Example 1 | 5.2 | 0.66 | 1.15 | 0.966 | B | C |
| Example 2 | 4.8 | 0.71 | 1.18 | 0.969 | B | C |
| Example 3 | 5.9 | 0.68 | 1.24 | 0.958 | B | C |
| Example 4 | 5.6 | 0.43 | 1.21 | 0.960 | B | C |
| Example 5 | 5.4 | 0.69 | 1.22 | 0.957 | B | C |
| Example 6 | 5.8 | 0.72 | 1.24 | 0.951 | B | C |
| Example 7 | 6.4 | 0.55 | 1.23 | 0.948 | B | C |
| Example 8 | 4.0 | 0.73 | 1.15 | 0.972 | B | B |
| Example 9 | 10.0 | 0.57 | 1.21 | 0.946 | B | B |
| Example 10 | 6.3 | 0.60 | 1.25 | 0.944 | B | B |
| Example 11 | 6.1 | 0.61 | 1.24 | 0.940 | B | B |
| Example 12 | 4.2 | 0.71 | 1.14 | 0.980 | B | B |
| Example 13 | 5.2 | 0.66 | 1.19 | 0.958 | B | C |
| Example 14 | 5.6 | 0.64 | 1.21 | 0.951 | B | C |
| Example 15 | 8.5 | 0.60 | 1.22 | 0.943 | B | B |
| Example 16 | 6.6 | 0.61 | 1.23 | 0.945 | B | B |
| Example 17 | 5.2 | 0.67 | 1.14 | 0.967 | B | C |
| Example 18 | 7.4 | 0.62 | 1.18 | 0.977 | B | B |
| Example 19 | 9.3 | 0.58 | 1.24 | 0.941 | B | C |
| Example 20 | 8.8 | 0.61 | 1.24 | 0.942 | B | C |
| Example 21 | 6.8 | 0.63 | 1.23 | 0.948 | B | C |
| Example 22 | 8.4 | 0.61 | 1.24 | 0.971 | B | B |
| Example 23 | 6.0 | 0.67 | 1.22 | 0.961 | B | B |

TABLE 2-continued

| | | | | | | |
|---|---|---|---|---|---|---|
| Example 24 | 5.3 | 0.68 | 1.16 | 0.974 | B | B |
| Example 25 | 5.0 | 0.69 | 1.15 | 0.977 | B | B |
| Example 26 | 5.7 | 0.65 | 1.16 | 0.975 | B | B |
| Example 27 | 5.2 | 0.66 | 1.15 | 0.966 | B | C |
| Example 28 | 5.7 | 0.68 | 1.29 | 0.857 | B | B |
| Example 29 | 5.4 | 0.66 | 1.42 | 0.895 | B | B |
| Example 30 | 5.2 | 0.67 | 1.16 | 0.967 | B | B |
| Example 31 | 6.9 | 0.79 | 1.24 | 0.940 | B | B |
| Comparative Example 1 | | Unable to granulate | | | A | A |
| Comparative Example 2 | | Unable to granulate | | | A | A |
| Comparative Example 3 | | Unable to granulate | | | A | A |
| Comparative Example 4 | | Unable to granulate | | | A | A |
| Comparative Example 5 | 27.8 | | A | 0.725 | B | A |
| Comparative Example 6 | 9.4 | | A | 0.784 | A | A |

According to the present invention, provided is additive manufacturing powder that can fabricate a laminate object having a complex solid free form with high mechanical strength and good dimension accuracy.

Having now fully described embodiments of the present invention, it will be apparent to one of ordinary skill in the art that many changes and modifications can be made thereto without departing from the spirit and scope of embodiments of the invention as set forth herein.

What is claimed is:

1. An additive manufacturing powder comprising:
   a core-shell type particle comprising
      a core particle comprising a first binder resin and a filler and
      a shell present on a surface of the core particle, the shell comprising a second binder resin,
   wherein the powder has a particle size distribution Dv/Dn of 1.5 or less where Dv is the volume average particle diameter and Dn is the number average particle diameter and an average circularity of 0.800 to 0.980,
   and wherein the additive manufacturing powder satisfies a relation: $0.2 \leq A/B < 0.8$, where A represents a volume average particle diameter of the filler and B represents a volume average particle diameter of the powder.

2. The additive manufacturing powder according to claim 1, wherein the filler accounts for 30 percent by weight or more of the powder.

3. The additive manufacturing powder according to claim 1, satisfying a relation: $0.43 \leq A/B \leq 0.72$.

4. The additive manufacturing powder according to claim 1, wherein the filler is at least one of a calcium phosphate based material or a carbon based material.

5. The additive manufacturing powder according to claim 4, wherein the filler is at least one of hydroxyapatite, α-tricalcium phosphate, β-tricalcium phosphate, or octacalcium phosphate.

6. The additive manufacturing powder according to claim 4, wherein the filler is at least one of carbon nanotube, graphene, or fullerene.

7. The additive manufacturing powder recording according to claim 1, wherein the powder has a volume average particle diameter Dv in a range of from 4.0 μm to 10.0 μm.

8. The additive manufacturing powder according to claim 1, wherein the powder has a particle size distribution Dv/Dn of 1.25 or less.

9. The additive manufacturing powder according to claim 1, wherein the powder has an average circularity in a range of from 0.940 to 0.980.

10. The additive manufacturing powder according to claim 1, wherein the second binder resin is incompatible with the first binder resin and swells to ethyl acetate.

11. The additive manufacturing powder according to claim 1, wherein the first binder resin is a polyester resin.

12. The additive manufacturing powder according to claim 1, wherein the second binder resin is a styrene-acrylic resin.

13. The additive manufacturing powder according to claim 1, wherein the first binder resin is a polyester resin and the second binder resin is a styrene-acrylic resin.

14. The additive manufacturing powder recording according to claim 1, wherein the powder has a volume average particle diameter Dv in a range of from 2.4 μm to 5.7 μm.

15. The additive manufacturing powder recording according to claim 1, wherein the filler is an inorganic material.

* * * * *